(12) United States Patent
Mobarak

(10) Patent No.: US 9,302,127 B2
(45) Date of Patent: Apr. 5, 2016

(54) DEODORANT WITH IMPROVED ENDURANCE AND STABILITY

(71) Applicant: Knowlton Development Corp. Inc., Knowlton (CA)

(72) Inventor: Hany Abo-El-Magd Mobarak, Milton (CA)

(73) Assignee: KNOWLTON DEVELOPMENT CORPORATION INC., Knowlton (CA)

( * ) Notice: Subject to any disclaimer, the term of this patent is extended or adjusted under 35 U.S.C. 154(b) by 182 days.

(21) Appl. No.: 13/788,554

(22) Filed: Mar. 7, 2013

(65) Prior Publication Data

US 2014/0255077 A1 Sep. 11, 2014

(51) Int. Cl.

| A61K 8/00 | (2006.01) |
|---|---|
| A61Q 15/00 | (2006.01) |
| A45D 40/00 | (2006.01) |
| A61K 8/19 | (2006.01) |
| A61K 8/97 | (2006.01) |
| A61K 8/34 | (2006.01) |
| A61K 8/36 | (2006.01) |
| A61K 8/73 | (2006.01) |

(52) U.S. Cl.
CPC ............... *A61Q 15/00* (2013.01); *A45D 40/00* (2013.01); *A61K 8/19* (2013.01); *A61K 8/345* (2013.01); *A61K 8/361* (2013.01); *A61K 8/732* (2013.01); *A61K 8/97* (2013.01)

(58) Field of Classification Search
CPC ....... A61Q 15/00; A61Q 17/04; A61Q 19/00; A61Q 13/00; A61Q 19/005; A61Q 17/005; A61Q 1/12; A61K 2300/00; A61K 2800/75; A61K 8/0229; A61K 2800/592; A61K 2800/10; A61K 31/00; A61K 8/0216; A61K 8/19; A61K 8/97; A61K 8/345; A61K 8/361; A61K 8/732; A23G 4/06; A23L 2/39; A45D 40/00
See application file for complete search history.

(56) References Cited

U.S. PATENT DOCUMENTS

| 2,980,246 A | 4/1961 | Leshin |
|---|---|---|
| 4,298,036 A | 11/1981 | Horvath |
| 4,521,127 A | 6/1985 | Romburo et al. |
| 4,617,185 A | 10/1986 | DiPietro |
| 4,621,935 A | 11/1986 | Sussman |
| 4,664,547 A | 5/1987 | Rosenwinkel |
| 4,743,444 A | 5/1988 | McCall |
| 4,915,528 A | 4/1990 | Seager |
| 4,950,094 A | 8/1990 | Yorks |
| 5,114,717 A | 5/1992 | Kuznitz et al. |
| 5,284,649 A | 2/1994 | Juneja |
| 5,326,185 A | 7/1994 | Dornbusch et al. |
| 5,376,363 A | 12/1994 | Benfatto et al. |
| 5,401,112 A | 3/1995 | Dornbusch et al. |
| 5,407,668 A | 4/1995 | Kellner |
| 5,424,070 A | 6/1995 | Kasat et al. |
| 5,516,510 A | 5/1996 | Beilfuss et al. |
| 5,635,164 A * | 6/1997 | Moghe et al. ................ 424/65 |
| 5,650,140 A | 7/1997 | Bergmann et al. |
| 5,650,141 A | 7/1997 | Bergmann et al. |
| 5,650,142 A | 7/1997 | Bergmann et al. |
| 5,650,143 A | 7/1997 | Bergmann et al. |
| 5,716,604 A | 2/1998 | Coe et al. |
| 5,736,574 A | 4/1998 | Burnier et al. |
| 5,863,524 A * | 1/1999 | Mason et al. ................ 424/65 |
| 5,897,263 A | 4/1999 | Fattori |
| 6,013,248 A | 1/2000 | Luebbe et al. |
| 6,071,028 A | 6/2000 | Klawson |
| 6,096,298 A | 8/2000 | Swaile |
| 6,123,932 A | 9/2000 | Guskey et al. |
| 6,165,480 A | 12/2000 | Kasat et al. |
| 6,174,521 B1 | 1/2001 | Li et al. |
| 6,435,748 B1 | 8/2002 | Taghikhani |
| 7,186,405 B2 | 3/2007 | Loffler et al. |
| 7,628,999 B2 * | 12/2009 | Sunkara ................ 424/401 |
| 8,029,812 B2 * | 10/2011 | Sunkara ................ 424/401 |
| 8,425,886 B2 | 4/2013 | Mobarak |
| 2005/0089488 A1 * | 4/2005 | Kim ........................ 424/65 |
| 2006/0029624 A1 | 2/2006 | Banowski et al. ............ 424/401 |
| 2007/0202062 A1 * | 8/2007 | Workman et al. ............ 424/66 |
| 2007/0202126 A1 | 8/2007 | Joerger et al. |
| 2007/0207113 A1 | 9/2007 | Joerger et al. |
| 2007/0241306 A1 | 10/2007 | Wehner et al. |
| 2007/0269392 A1 * | 11/2007 | Sunkara ................ 424/59 |
| 2008/0095809 A1 | 4/2008 | Moghe et al. |
| 2008/0241089 A1 * | 10/2008 | Banowski et al. ............ 424/65 |
| 2008/0292560 A1 * | 11/2008 | Tamarkin et al. ............ 424/45 |
| 2008/0292571 A1 | 11/2008 | Kim |
| 2009/0169500 A1 * | 7/2009 | Sunkara ................ 424/65 |
| 2010/0047296 A1 * | 2/2010 | Banowski et al. ............ 424/401 |
| 2011/0033405 A1 * | 2/2011 | Mobarak ................ 424/65 |

* cited by examiner

*Primary Examiner* — Robert A Wax
*Assistant Examiner* — Olga V Tcherkasskaya
(74) *Attorney, Agent, or Firm* — Gowling WLG (Canada) LLP

(57) ABSTRACT

The present invention provides an improved deodorant formulation having good efficacy and excellent stability. The deodorant formulation comprises propanediol combined with zinc ricinoleate, grapefruit seed extract, and sodium bicarbonate as the principal deodorizing actives. The combination of these deodorizing active ingredients results in a formulation with strong efficacy which lasts at least 24 hours. The deodorant formulation also displays improved stability when formed into a solid stick product. These features combined provide for an improved deodorant formulation having excellent features of efficacy and stability.

19 Claims, 10 Drawing Sheets

FIGURE 1

Sample Formulation

| Material | % (w/w) |
|---|---|
| Propanediol | 30.0% |
| Glycerin | 30.0% |
| Sodium Stearate | 8.0% |
| Zinc ricinoleate | 2.5% |
| Polyglyceryl-3-caprate | 0.5% |
| Silica | 0.9% |
| Grapefruit Seed Extract | 0.1% |
| Allantoin | 0.2% |
| Sucrose Cocoate | 0.9% |
| Corn (zea mays) starch | 0.9% |
| Sodium bicarbonate | 0.1% |
| Water | q.s. |
| Essential oils/perfumes | q.s. |
| | 100.0% |

FIGURE 2

Efficacy Panel Test – 10 Point Armpit Odour Intensity Grading Scale

| 0 | 2 | 4 | 6 | 8 | 10 |
|---|---|---|---|---|---|
| Odour absent | Odour barely perceptible | Odour definitely perceptible | Odour Moderate | Odour strong | Odour very strong |

FIGURE 3A

Individual Odour Scores of 20 subjects at T0

Treated Armpit

| #Vol. | Judge #1 | Judge #2 | Judge #3 | Average T | STDEV |
|---|---|---|---|---|---|
| 1 | 1.5 | 2 | 5 | 2.8 | 1.9 |
| 2 | 3 | 6 | 3 | 4.0 | 1.7 |
| 3 | 3 | 3 | 2 | 2.7 | 0.6 |
| 4 | 5 | 2 | 3 | 3.3 | 1.5 |
| 5 | 4 | 4 | 4 | 4.0 | 0.0 |
| 6 | 2 | 3 | 2 | 2.3 | 0.6 |
| 7 | 3 | 4 | 4 | 3.7 | 0.6 |
| 8 | 8 | 5 | 6 | 6.3 | 1.5 |
| 9 | 6 | 5 | 8 | 6.3 | 1.5 |
| 10 | 7 | 5 | 6 | 6.0 | 1.0 |
| 11 | 7 | 7 | 6 | 6.7 | 0.6 |
| 12 | 4 | 5 | 4 | 4.3 | 0.6 |
| 13 | 3 | 4 | 2 | 3.0 | 1.0 |
| 14 | 8 | 4 | 8 | 6.7 | 2.3 |
| 15 | 8 | 5 | 6 | 6.3 | 1.5 |
| 16 | 8 | 4 | 6 | 6.0 | 2.0 |
| 17 | 8 | 7 | 8 | 7.7 | 0.6 |
| 18 | 2 | 3 | 2 | 2.3 | 0.6 |
| 19 | 6 | 4 | 4 | 4.7 | 1.2 |
| 20 | 8 | 6 | 8 | 7.3 | 1.2 |
| Mean Value | | | | 4.8 | 1.1 |

Control Armpit

| #Vol. | Judge #1 | Judge #2 | Judge #3 | Average T | STDEV |
|---|---|---|---|---|---|
| 1 | 3 | 2 | 3 | 2.7 | 0.6 |
| 2 | 4 | 5 | 2 | 3.7 | 1.5 |
| 3 | 3 | 3 | 3 | 3.0 | 0.0 |
| 4 | 5 | 1 | 3 | 3.0 | 2.0 |
| 5 | 3 | 3 | 3 | 3.0 | 0.0 |
| 6 | 2 | 2 | 2 | 2.0 | 0.0 |
| 7 | 4 | 3 | 4 | 3.7 | 0.6 |
| 8 | 8 | 4 | 8 | 6.7 | 2.3 |
| 9 | 7 | 4 | 8 | 6.3 | 2.1 |
| 10 | 8 | 5 | 5 | 6.0 | 1.7 |
| 11 | 7 | 7 | 6 | 6.7 | 0.6 |
| 12 | 4 | 5 | 4 | 4.3 | 0.6 |
| 13 | 4 | 4 | 2 | 3.3 | 1.2 |
| 14 | 8 | 5 | 6 | 6.3 | 1.5 |
| 15 | 6 | 3 | 8 | 5.7 | 2.5 |
| 16 | 10 | 4 | 6 | 6.7 | 3.1 |
| 17 | 8 | 7 | 7 | 7.3 | 0.6 |
| 18 | 4 | 2 | 2 | 2.7 | 1.2 |
| 19 | 4 | 3 | 4 | 3.7 | 0.6 |
| 20 | 8 | 4 | 6 | 6.0 | 2.0 |
| Mean Value | | | | 4.6 | 1.2 |

FIGURE 3B

Individual Odour Scores of 20 subjects at 18h

Treated Armpit

| #Vol. | Judge #1 | Judge #2 | Judge #3 | Average T | STDEV |
|---|---|---|---|---|---|
| 1 | 1 | 1 | 1 | 1.0 | 0.0 |
| 2 | 1 | 2 | 1 | 1.3 | 0.6 |
| 3 | 2 | 2 | 2 | 2.0 | 0.0 |
| 4 | 2 | 1 | 1 | 1.3 | 0.6 |
| 5 | 0 | 3 | 2 | 1.7 | 1.5 |
| 6 | 1 | 3 | 2 | 2.0 | 1.0 |
| 7 | 1 | 2 | 1 | 1.3 | 0.6 |
| 8 | 4 | 2 | 4 | 3.3 | 1.2 |
| 9 | 6 | 2 | 4 | 4.0 | 2.0 |
| 10 | 4 | 1 | 3 | 2.7 | 1.5 |
| 11 | 4 | 3 | 6 | 4.3 | 1.5 |
| 12 | 2 | 3 | 3 | 2.7 | 0.6 |
| 13 | 2 | 2 | 4 | 2.7 | 1.2 |
| 14 | 6 | 2 | 4 | 4.0 | 2.0 |
| 15 | 4 | 2 | 7 | 4.3 | 2.5 |
| 16 | 6 | 2 | 4 | 4.0 | 2.0 |
| 17 | 4 | 2 | 6 | 4.0 | 2.0 |
| 18 | 4 | 1 | 3 | 2.7 | 1.5 |
| 19 | 4 | 2.5 | 3 | 3.2 | 0.8 |
| 20 | 4 | 0 | 4 | 2.7 | 2.3 |
| Mean Value | | | | 2.8 | 1.3 |

Control Armpit

| #Vol. | Judge #1 | Judge #2 | Judge #3 | Average T | STDEV |
|---|---|---|---|---|---|
| 1 | 1 | 1 | 2 | 1.3 | 0.6 |
| 2 | 3 | 4 | 3 | 3.3 | 0.6 |
| 3 | 2 | 1 | 3 | 2.0 | 1.0 |
| 4 | 6 | 2 | 4 | 4.0 | 2.0 |
| 5 | 1 | 2 | 2 | 1.7 | 0.6 |
| 6 | 1 | 2 | 2 | 1.7 | 0.6 |
| 7 | 1 | 0 | 1 | 0.7 | 0.6 |
| 8 | 2 | 4 | 6 | 4.0 | 2.0 |
| 9 | 8 | 1 | 4 | 4.3 | 3.5 |
| 10 | 8 | 1 | 6 | 5.0 | 3.6 |
| 11 | 6 | 5 | 8 | 6.3 | 1.5 |
| 12 | 2 | 3 | 3 | 2.7 | 0.6 |
| 13 | 4 | 2 | 7 | 4.3 | 2.5 |
| 14 | 2 | 7 | 6 | 5.0 | 2.6 |
| 15 | 5 | 4 | 7 | 5.3 | 1.5 |
| 16 | 6 | 4 | 6 | 5.3 | 1.2 |
| 17 | 4 | 5 | 7 | 5.3 | 1.5 |
| 18 | 6 | 3 | 2 | 3.7 | 1.2 |
| 19 | 6 | 5 | 3 | 4.7 | 1.5 |
| 20 | 8 | 4 | 6 | 6.0 | 2.0 |
| Mean Value | | | | 3.8 | 1.6 |

FIGURE 3C

Individual Odour Scores of 20 subjects at T16h

Treated Armpit

| #Vol. | Judge #1 | Judge #2 | Judge #3 | Average T | STDEV |
|---|---|---|---|---|---|
| 1 | 1 | 0 | 1 | 0.7 | 0.6 |
| 2 | 1 | 2 | 1 | 1.3 | 0.6 |
| 3 | 2 | 2 | 1 | 1.7 | 0.6 |
| 4 | 1 | 1 | 1 | 1.0 | 0.0 |
| 5 | 0 | 1 | 1 | 0.7 | 0.6 |
| 6 | 1 | 1 | 1 | 1.0 | 0.0 |
| 7 | 1.5 | 0.5 | 1 | 1.0 | 0.5 |
| 8 | 4 | 3 | 3 | 3.3 | 0.6 |
| 9 | 4 | 4 | 6 | 4.7 | 1.2 |
| 10 | 4 | 2 | 3 | 3.0 | 1.0 |
| 11 | 4 | 4 | 3 | 3.7 | 0.6 |
| 12 | 4 | 2 | 3 | 3.0 | 1.0 |
| 13 | 2 | 6 | 4 | 4.0 | 2.0 |
| 14 | 6 | 2 | 4 | 4.0 | 2.0 |
| 15 | 4 | 0.5 | 5 | 3.2 | 2.4 |
| 16 | 4 | 4 | 7 | 5.0 | 1.7 |
| 17 | 6.5 | 2 | 6 | 4.8 | 2.5 |
| 18 | 4 | 0 | 2 | 2.0 | 2.0 |
| 19 | 6 | 2 | 2 | 3.3 | 2.3 |
| 20 | 8 | 4.5 | 7 | 6.5 | 1.8 |
| Mean Value | | | | 2.9 | 1.2 |

Control Armpit

| #Vol. | Judge #1 | Judge #2 | Judge #3 | Average T | STDEV |
|---|---|---|---|---|---|
| 1 | 1 | 0.1 | 2 | 1.0 | 1.0 |
| 2 | 4 | 4 | 4 | 4.0 | 0.0 |
| 3 | 2 | 1 | 3 | 2.0 | 1.0 |
| 4 | 4 | 3 | 3 | 3.3 | 0.6 |
| 5 | 1.5 | 3 | 2 | 2.2 | 0.8 |
| 6 | 2 | 3 | 2 | 2.3 | 0.6 |
| 7 | 1 | 2 | 2 | 1.7 | 0.6 |
| 8 | 2 | 3 | 5 | 3.3 | 1.5 |
| 9 | 8 | 3 | 4 | 5.0 | 2.6 |
| 10 | 8 | 3 | 6 | 5.7 | 2.5 |
| 11 | 8 | 3 | 3 | 4.7 | 2.9 |
| 12 | 2 | 2 | 2 | 2.0 | 0.0 |
| 13 | 4 | 4 | 6 | 4.7 | 1.2 |
| 14 | 2 | 6.5 | 6 | 4.8 | 2.5 |
| 15 | 6 | 4 | 7 | 5.7 | 1.5 |
| 16 | 6 | 2 | 8 | 5.3 | 3.1 |
| 17 | 4 | 6 | 6 | 5.3 | 1.2 |
| 18 | 6 | 2 | 2 | 3.3 | 2.3 |
| 19 | 6 | 6 | 3 | 5.0 | 1.7 |
| 20 | 8 | 6 | 8 | 7.3 | 1.2 |
| Mean Value | | | | 3.9 | 1.4 |

FIGURE 3D

Individual Odour Scores of 20 subjects at T24h

Treated Armpit

| #Vol. | Judge #1 | Judge #2 | Judge #3 | Average T | STDEV |
|---|---|---|---|---|---|
| 1 | 1 | 1 | 1 | 1.0 | 0.0 |
| 2 | 4 | 6 | 1 | 3.7 | 2.5 |
| 3 | 2 | 2 | 1 | 1.7 | 0.6 |
| 4 | 3 | 1 | 2 | 2.0 | 1.0 |
| 5 | 0 | 1 | 1 | 0.7 | 0.6 |
| 6 | 5 | 1 | 3 | 3.0 | 2.0 |
| 7 | 4 | 0 | 2 | 2.0 | 2.0 |
| 8 | 4 | 3 | 6 | 4.3 | 1.5 |
| 9 | 8 | 5 | 9 | 7.3 | 2.1 |
| 10 | 6 | 3 | 6 | 5.0 | 1.7 |
| 11 | 4 | 2 | 2 | 2.7 | 1.2 |
| 12 | 6 | 2 | 4 | 4.0 | 2.0 |
| 13 | 2 | 4 | 5 | 3.7 | 1.5 |
| 14 | 4 | 2 | 2 | 2.7 | 1.2 |
| 15 | 6 | 2 | 7 | 5.0 | 2.6 |
| 16 | 6 | 5 | 7 | 6.0 | 1.0 |
| 17 | 8 | 3 | 8 | 6.3 | 2.9 |
| 18 | 4 | 0 | 3 | 2.3 | 2.1 |
| 19 | 4 | 2 | 4 | 3.3 | 1.2 |
| 20 | 8 | 7 | 8 | 7.7 | 0.6 |
| Mean Value | | | | 3.7 | 1.5 |

Control Armpit

| #Vol. | Judge #1 | Judge #2 | Judge #3 | Average T | STDEV |
|---|---|---|---|---|---|
| 1 | 2 | 0 | 4 | 2.0 | 2.0 |
| 2 | 4 | 4 | 4 | 4.0 | 0.0 |
| 3 | 2 | 1 | 3 | 2.0 | 1.0 |
| 4 | 5 | 5 | 4 | 4.7 | 0.6 |
| 5 | 3 | 3 | 3 | 3.0 | 0.0 |
| 6 | 2 | 4 | 3 | 3.0 | 1.0 |
| 7 | 1 | 3 | 2 | 2.0 | 1.0 |
| 8 | 4 | 4 | 8 | 5.3 | 2.3 |
| 9 | 7 | 7 | 4 | 6.7 | 1.5 |
| 10 | 8 | 4 | 8 | 6.3 | 2.1 |
| 11 | 8 | 7 | 4 | 6.3 | 2.1 |
| 12 | 4 | 2 | 3 | 3.0 | 1.0 |
| 13 | 4 | 6 | 8 | 6.0 | 2.0 |
| 14 | 2 | 3.5 | 2 | 2.5 | 0.9 |
| 15 | 8 | 4.5 | 8 | 6.8 | 2.0 |
| 16 | 8 | 2 | 8 | 6.0 | 3.5 |
| 17 | 9 | 9 | 9 | 9.0 | 0.0 |
| 18 | 6 | 2 | 4 | 4.0 | 2.0 |
| 19 | 4 | 4.5 | 4 | 4.2 | 0.3 |
| 20 | 8 | 8 | 9 | 8.3 | 0.6 |
| Mean Value | | | | 4.9 | 1.3 |

FIGURE 4

Averaged Odour Scores for Treated Armpit v. Control Armpit

| | Treated Armpit | | | | Control Armpit | | | |
|---|---|---|---|---|---|---|---|---|
| Time | $T_0$ | 8 hr | 16 hr | 24 hr | $T_0$ | 8 hr | 16 hr | 24 hr |
| Score | 4.8 | 2.8 | 2.9 | 3.7 | 4.6 | 3.8 | 3.9 | 4.8 |
| % Reduction in Odour | - | 42% | 40% | 23% | - | 17% | 15% | -4% |

12-Week Stability Test Results at 25°C for Prior Art v. Invented Deodorant Formulation

| Week | 0 | 2 | 4 | 6 | 8 | 10 | 12 |
|---|---|---|---|---|---|---|---|
| Prior Art Formulation | 0.00% | 0.19% | 0.42% | 0.63% | 1.02% | 1.37% | 1.54% |
| Invented Formulation | 0.00% | 0.02% | 0.05% | 0.07% | 0.08% | 0.26% | 0.12% |

12-Week Stability Test Results at 45°C for Prior Art v. Invented Deodorant Formulation

| Week | 0 | 2 | 4 | 6 | 8 | 10 | 12 |
|---|---|---|---|---|---|---|---|
| Prior Art Formulation | 0.00% | 0.30% | 0.87% | 1.72% | 2.49% | 3.43% | 4.20% |
| Invented Formulation | 0.00% | 0.06% | 0.12% | 0.18% | 0.24% | 0.31% | 0.36% |

DEODORANT WITH IMPROVED ENDURANCE AND STABILITY

FIELD OF THE INVENTION

The present invention relates to a novel solid deodorant formulation which displays efficacy for longer periods, and has improved stability when made into a solid stick form.

BACKGROUND OF THE INVENTION

Topical deodorant formulations for use in controlling odour in the underarm area have been available in the market for many years, containing deodorizing active ingredients that generally work by inhibiting bacterial growth, masking odours, or by chemically fixing undesirable odours. One significant challenge with deodorant formulations has been to obtain longer lasting effect. Many formulations work well immediately following application or for a few hours afterward. However, as time passes following application, many formulations have not been able to offer sustained protection against odour. Because users typically apply deodorants after bathing in the morning, and may not have the opportunity to reapply until the next morning, it is desirable to have a deodorant which can provide odour control for a full 24 hours following application.

The longevity of deodorant effect, while important, is not the only feature that is needed in a commercially acceptable deodorant formulation. For deodorants which will be made into solid stick forms for use by the consumer, stability and shelf life is also important. Deodorant sticks, over time, tend to suffer weight loss due to the condensing out of moisture from the stick. Moisture typically rises to the surface of the solid. The moisture can then evaporate, which results in a shrunken, hardened product that pulls away from the container wall, or the moisture may stay on the surface of the deodorant stick, which may result in a product with a mushy, moisture-logged surface. In either case, the result is product which spoils over periods of storage. Manufacturers must therefore specify relatively early "best-before" dates on the products to reduce the risk that a consumer purchases a product past its prime. Expired deodorants must also be replaced with new stock. It would be advantageous to have a deodorant formulation which is stable for a longer time following manufacture, so that the resulting products may be stored and salable for longer.

In addition to the above issues, consumers are becoming ever more conscious of the ingredients in their personal care products. There is increasing demand for products which have been formulated with natural ingredients which are not synthetically derived, and which can be formulated with minimal environmental impact. Many consumers are also cautious of ingredients used in deodorants that have been shown to be carcinogens, such as triclosan, or ingredients that are petroleum-derived, such as propylene glycol.

The need for naturally formulated deodorant products with good efficacy which can be sustained for longer periods of time, combined with the better stability and shelf-life required for a commercial product, has posed challenges to manufacturers. There are some such deodorant formulations available which claim efficacy over 24 hours, but the stability of these formulations has been compromised. Chemists in this field have found that it is much more difficult to formulate efficacious and stable deodorants when one is limited to using natural ingredients.

What is needed is a solid stick deodorant formulation, that preferably contains all natural or naturally sourced ingredients, which shows efficacy for a longer time following application, and is also stable for a longer time once formed into a deodorant stick product.

SUMMARY OF THE INVENTION

The present invention provides an improved natural deodorant formulation that exhibits the desirable features of excellent efficacy combined with stability when formulated into stick form. The clinical efficacy testing demonstrates that this product can provide significant deodorizing activity even 24 hours after application. This deodorant when formulated into stick form also has significantly increased stability, and therefore increased shelf life and commercial value.

In one embodiment the invention comprises a novel deodorant formulation having propanediol as the base, combined with the deodorizing active materials zinc ricinoleate, grapefruit seed extract, and sodium bicarbonate. It has been found that the combination of propanediol, grapefruit seed extract, zinc ricinoleate, and sodium bicarbonate when applied topically to the skin, provides effective deodorizing effect which is longer lasting, with significant effect still present 24 hours following application. When manufactured into solid stick deodorant product which is filled through the top of a container in accordance with the process outlined herein, a deodorant stick product displaying excellent efficacy and stability is formed.

BRIEF DESCRIPTION OF THE FIGURES

The present invention will now be better understood with reference to the description and to the accompanying figures in which:

FIG. 1 is a table outlining a sample deodorant stick formulation in accordance with the invention;

FIG. 2 is a table showing the 10 point odour intensity grading scale by which the efficacy of the deodorant in reducing odour was assessed;

FIG. 3A is a table summarizing the results of efficacy testing of 20 subjects before application of the tested product;

FIG. 3B is a table summarizing the results of efficacy testing of the 20 subjects at 8 hours after application;

FIG. 3C is a table summarizing the results of efficacy testing of the 20 subjects at 16 hours after application;

FIG. 3D is a table summarizing the results of efficacy testing of the 20 subjects at 24 hours after application;

FIG. 4 is a table summarizing the averaged results of the efficacy testing for the 20 subjects;

DETAILED DESCRIPTION OF THE EMBODIMENTS

Figure 5:
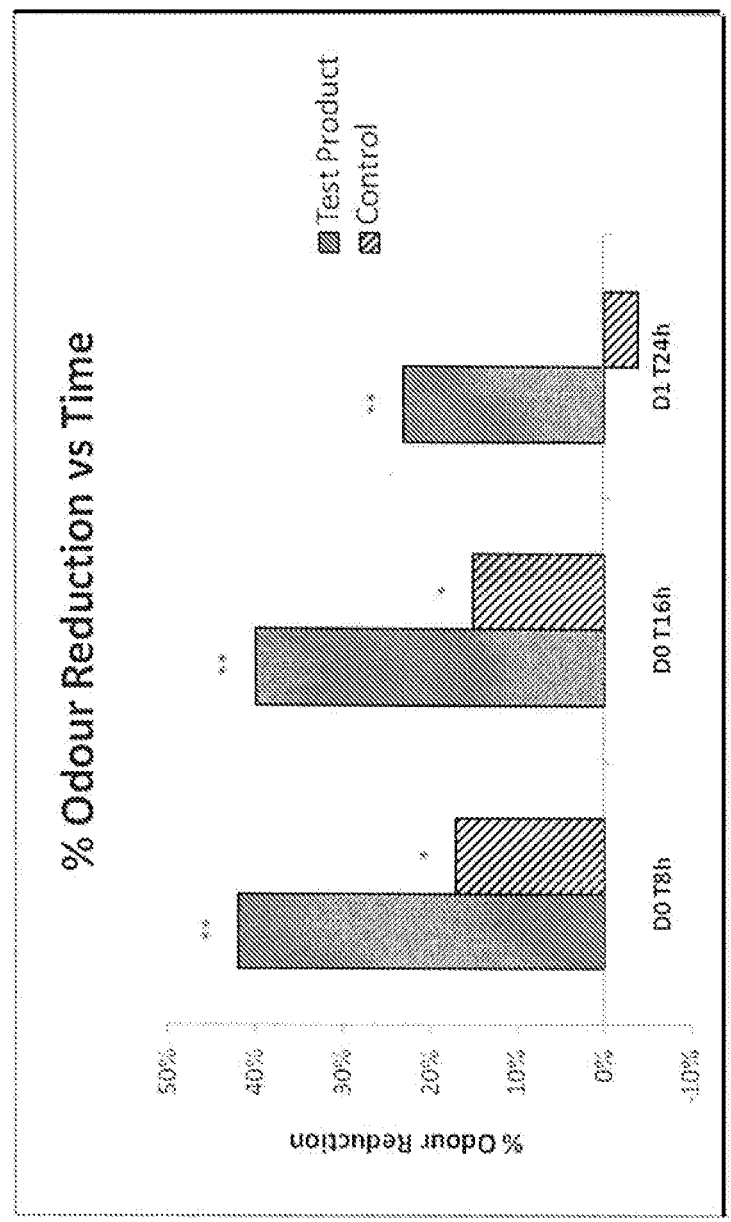
FIG. 5 is a graph demonstrating the efficacy of the invented formulation, in which percent odour reduction over time is shown for the invented formulation versus the control.

The present invention relates to a deodorant formulation that shows good efficacy even at 24 hours following application, and excellent stability when formed into a solid stick product.

The ingredients used in the deodorant composition of the invention are preferably natural, or substantially natural, ingredients. In the deodorant industry, the term "natural" generally indicates that the ingredient is derived from a plant or other sustainable source. This is in contrast to synthetic chemicals or those derived from petroleum.

In a first embodiment, the deodorant composition comprises propanediol (chemical name: 1,3-propanediol), combined with deodorizing active ingredients, namely zinc ricinoleate, grapefruit seed extract and sodium bicarbonate. Each of these ingredients are known in the art and available from a number of sources. For example, the propanediol used is commercially available from DUPONT™ under the trademark ZEMEA™. ZEMEA™ is particularly beneficial to use in a natural deodorant formulation as it is a biodegradable product that is manufactured from corn with reduced environmental impact, using 40% less energy in the manufacturing process as compared with a petroleum-based propanediol (chemical name: 1,2-propanediol).

Zinc ricinoleate is a salt of ricinoleic acid, which is derived from castor seed oil. It is a deodorizing active ingredient which is believed to work by chemically fixing odour molecules, such as those known to be formed by bacteria present on the skin following perspiration. Grapefruit seed extract is also a known natural deodorizing active ingredient with antibacterial properties, which is made by converting grapefruit seeds and pulp into acidic liquid. Sodium bicarbonate is a well known deodorizing substance with proven antimicrobial properties.

There are hundreds of other options for deodorizing active ingredients for use in cosmetic formulations such as stick deodorants. While each of the above ingredients are known generally to have activity as deodorizing agents, they have not been known to stand out as particularly effective deodorizing agents as compared to other available agents. However, as detailed below, the inventor has found that the combination of these ingredients in a deodorant composition gives high levels of deodorant activity which can last at least 24 hours.

In addition to the above three deodorizing active ingredients, additional ingredients may be incorporated in the deodorant formulation. For example, vegetable glycerin may be included as a solvent ingredient for water-soluble components of the formulation, and to contribute structure to the solidified product. In addition to propanediol, other polymeric or non-polymeric alcohols may be included. Other ingredients that may be used, include but are not limited to, quantities of diethylene glycol, triethylene dipropylene glycol, tripropylene glycol, tetrapropylene glycol, tetraethylene glycol, dibutylene glycol, diethylene glycol, monoethylether, PEG-8, 1,3-butanediol, 1,4-butanediol, glycerol propoxylate, dipropylene glycol, tripropylene glycol, tetrapropylene glycol, hexylene glycol, 1,2-hexanediol, 1,3-butylene glycol, 1,2,5-trihyroxyhexane, 1,2,3-trihydroxyhexane, hexylene glycol, and 1,2-henediol.

Another ingredient that may be included is a gelling agent, also known in the field as a structurant. A particularly preferred and common gelling agent used in solid deodorant formulations is sodium stearate. Other optional gelling agents which may be used include, but are not limited to glyceryl laurate, beeswax, colloids, cocoa butter, shea butter, mango butter, hydrogenated vegetable oils, sodium oleate, sodium palmitate, sodium laurate, sodium arachidate, sodium behenate, potassium stearate, potassium palmitate, sodium myristate, aluminum monostearate, 16-hydroxyhexadecanoyl acid, fatty acid amides, fatty acid alkanol amides, dibenzalsorbitol, alkyl amides of citric acids, tricarballylic acid, aconitic acid, nitrilotriacetic acid, succinic acid, 2-hydroxy-1,2,3-propane tributylamide, 1-propene-1,2,3-trioctylamide, N,N',N"-tri (acetodecylamide) amine, 2-dodecyl-N,N'-dihexylsuccinamide, 2-dodecyl-N,N'-dibutylsuceinamide, dimethylamine stearate, triethylamine stearate, triethylemine oleate, diethylamine stearate, and trimethylamine oleate.

Emulsifiers may also be included in the formulation. Polyglyceryl-3-caprate is an emulsifier with excellent properties for incorporation in cosmetics and deodorants. Sucrose cocoate is another emulsifier that is also a beneficial ingredient in preparations intended for the skin as it also acts as an emollient. Other options include non-volatile saturated fatty alcohols such as benehyl alcohol, cetearyl alcohol and cetearyl glucoside, inulin lauryl carbamate, citric acid esters, sorbitan esters of fatty acids, other polyglycerol esters of fatty acids, saponins, lecithins, and carageenan.

Starch may also be added to the formulation, principally to improve the texture and feel of the solid product. Types of starch that may be used in the formulations of the invention include, but are not limited to, corn (*Zea Mays*) starch and distarch phosphate acetate. Similarly, the addition of silica imparts a drier feeling to the applied product. The addition of allantoin makes the composition moisturizing and beneficial for the skin.

Additional deodorizing actives may be included with those specified above. There are hundreds of other ingredients with such properties, including, but not limited to: alpha bisabolol, benzoic acid, rosemarinic acid, caffeic acid, camosic acid, ferrulic acid, galic acid, perillic acid, glucose methyl rapesseedate ferment, C12-13 alkyl lactate, chitosan, hinokitiol, eucalyptol, linalool, limonene, geraniaol, citral, benzyl benzoate, citronella sodium citronellate, citronellyl methylcrotonate, coumarin, engenool, benzyl salicylate, alum, farnesol, glucose oxidase, lactoperoxidase, glycerin monolaurate, levulinic acid, nisin, phenoxyethanol, potassium sorbate, isostearic acid, sodium usnate, tea tree, cetyltrimethylammonium bromide, cetyl pyridinium chloride, benzethonium chloride, diisobutyl phenoxy ethoxy ethyl dimeethyl benzyl ammonium chloride, sodium N-palmethyl sarcosine, N-myristoyl glycine, potassium N-lauryl sarcosine, trimethyl ammonium chloride, sodium aluminum chlorohydroxy lactate, triethyl citrate, triclocarban, diaminoalkyl amides such as L-lysine hexadecyl amide, heavy metal salts of citrate, salicylate, and piroctose, polyglyceryl-3-caprylate, zinc phenolsulfate, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-myristoyl glycine, potassium N-lauroyl sarcosine, stearyl trimethyl ammonium chloride, cetyltrimethylammonium chloride, cetylpyridinium chloride, diisobutyl-ethyoxyethyldimenethylbenzelammonium chloride, sodium N-laurylsarcosinate, sodium-N-palmethylsarcosinate, N-myristoylglycine, potassium N-laurylsarcosine, trimethylammonium chloride, sodium aluminum chiorohydroxylactate, triethyl citrate, tricetylmethylammonium chloride, triclosan, phenoxyethanol, 1,5-pentanediol, 1,6-hexandediol, diaminoalkylamide (eg. 1-lysine hexadecyl amide, citrate heavy metal sales, salicylates, piroctoses, zinc phenolsulfonate, dichloro-m-xylenol, 2,2'-methylenebis(3,4,6-trichlorophenol), 2,2'-thiobis(4,6-dichloropheol), p-chloro-m-zelenol, dichloro-m-xylenol, phenethyl alcohol, and any of the alkalirhodanides.

In addition, malodor masking agents such as perfumes and fragrances may be incorporated. Again, there are many options known in the art that have been used in cosmetic formulations, and which include, but are not limited to any essential oils or perfumes such as florals, herbs, fruits, trees, shrubs, fungi, corals, grasses such as rosewood, lavender, litsea cubeba, tea tree, lemon, lime, orange, petitgrain, geranium, lemongrass, palmarosa, mandarin, coriander, rose, patchouli, yarrow, cypress, cedar, citronella, bergamot, pine, myrtle, cypress, orange blossom, pine oil, citrus oil, jasmine oil, lily oil, rose oil, ylang ylang oil, sage oil, chamomile oil, oil of cloves. Melissa oil, mint oil, cinnamon leaf oil, lime blossom oil, juniper berry oil, vetiver oil, iolibanum oil, galbanum oil, laudanum oil, resins such as benzoin siam resinoid and opoponax resinoid, benzyl acetate, phenoxyethyl isobutyrate, p-tert-butylcyclohexyl acetate, linalyl acetate, diva acetate, phenylethyl acetate, linalyl benzoate, benzeyl formate, ethyl methylphenylglycinate, allyl cyclobexylpropionate, styrallyl propionate, benzyl salicylate, benzyl ethyl ether, citral, citronellal, citronellyloxyacetaldehyde, cyclamenaldehyde, hydroxycitronellal, lilial, bourgeonal, ionones, anethole, citronellol, eugenool, geraniol, linalool, phenylethyl alcohol, terpineol, isoamyl salicylate, benzyl salicylate, thyme oil red, B-methyl naphthyl ketone, p-t-butyl-A-methyl hydrocinnamic aldehyde, p-t-amyl cyclohexanone, coumarin, B-naphthyl methyl ether, diethyl phthalate, phenylethyl phenylacetate, dimurcetol, phenylethyl alcohol, undecyl aldehyde, undecylenic aldehyde, lauric aldeheyde, amyl cinnamic aldehyde, ethyl methyl phenyl glycidate, methyl nonyl aldehyde, octyl aldehyde, undecalactone, hexyl cinnamic aldehyde, benzaldehyde, vanillin, heliotropine, camphor, parahydroxy phenolbutannone, 6-acetyl 1,1,3,4,4,6 hexamethyl tetrahydronaphtahalene, alpha-methyl ionone, gamma-methyl ionone, amyl-cyclohexanone, linalyl acetate, isopropyl mystirate, cedryl acetate, and myrcenyl acetate.

As will be understood from the description provided herein, in one embodiment the present invention provides a deodorant formulation comprising by weight, based on the total weight of the composition: from about 30-60% propanediol; from about 1.5-3% zinc ricinoleate; from about 0.1-2% grapefruit seed extract; and from about 0.05-0.2% sodium bicarbonate. It will be understood that the use of the term "about" in relation to a range applies to both ends of the range provided.

In another embodiment, the deodorant formulation further comprises at least one of a gelling agent, an emulsifier, starch, further deodorizing active ingredients, and mixtures thereof.

In an alternative embodiment, the deodorant formulation comprises, by weight based on the total weight of the composition: 30-60% propanediol; from about 20-40% glycerin; from about 1.5-3% zinc ricinoleate; from about 0.1-2% grapefruit seed extract; from about 0.05-0.2% sodium bicarbonate; from about 5-10% gelling agent; from about 05-3% of an emulsifier; from about 0.5-4% silica; from about 0.5-6% starch; from about 0.1-1% allantoin; and from about 0.001-5% of one or more further deodorizing active ingredients.

In a further embodiment, the deodorant formulation comprises, by weight based on the total weight of the composition: 30-60% propanediol; from about 20-40% glycerin; from about 1.5-3% zinc ricinoleate; from about 0.1-2% grapefruit seed extract; from about 0.05-0.2% sodium bicarbonate; from about 5-10% sodium stearate; from about 0.5-2% polyglyceryl-3-caprate; from about 0.1-1% sucrose cocoate; from about 0.5-4% silica; from about 0.5-6% corn starch; from about 0.1-1% allantoin; from about 20-30% water; and from about 0.001-5% of one or more further deodorizing active ingredients.

In a further embodiment, the deodorant formulation comprises, by weight based on the total weight of the composition: from about 30% propanediol; from about 30% glycerin; from about 2.5% zinc ricinoleate; from about 0.1% grapefruit seed extract; from about 0.1% sodium bicarbonate; from about 8% sodium stearate; from about 0.5% polyglyceryl-3-caprate; from about 0.9% sucrose cocoate; from about 0.9% silica; from about 0.9% corn starch; from about 0.2% allantoin; water q.s.; and essential oils and/or perfumes q.s.

A sample formulation of the invention, as shown in FIG. 1, displays excellent efficacy. In the industry, efficacy testing for deodorants is typically conducted by way of panel studies, in which the test substances and control substances are applied to the axilla of human subjects, and odour is then assessed at intervals by an objective panel of reviewers. This type of deodorant testing is referred to in the industry as a "sniff test". Such a sniff test was conducted in this case, involving twenty subjects and three judges. Each subject's two armpits were tested using one as a control (which was untreated), and one having application of the invented deodorant formulation. The testing conformed with the standard specified in ASTM International Standard E1207-09, being randomized and single-blinded; judges were blinded to the identity of the control and treated armpits.

As seen in FIG. 2, the twenty subjects were tested using a 10-point subjective axillary odour scale, with a ranking of 0 indicating no odour, and a ranking of 10 indicating a very strong sweaty odour. Middle rankings of 4 to 6 indicated definitely perceptible to moderate odours.

As set out respectively in FIGS. 3A-3D, subjects were tested prior to treatment (Day 0-T0), and at intervals of Day 0-8 hours, Day 0-16 hours, and Day 1-24 hours post-treatment. The mean results for the twenty subjects are presented in FIG. 4. The values demonstrate that the deodorant formulation of the invention was effective at neutralizing axillary odour. At each of 8, 16, and 24 hours post-treatment, the percent odour reduction was significant, ranging from 25 to 27% odour reduction. The differences between treated and control armpits of the subjects were found to be statistically significant.

The panel testing results summarized in FIG. 4 show 24 hour efficacy for the deodorant formulation of the invention. This level of odour reduction is excellent and long-lasting, and has not been seen for a deodorant formulation containing substantially natural ingredients when combined with the features of stability described below.

Further testing demonstrates that when formulated into stick products made in accordance with a "top-fill" method (described generally following), the deodorant formulation has excellent stability. The general manufacturing process for creating such deodorant stick products is known. The water-soluble ingredients are progressively added and mixed under agitation, while heating to temperatures suitable to promote the dissolution of the ingredients. The mixture is then cooled while continuing to be agitated. Volatile ingredients such as essential oils, perfumes, and the grapefruit seed extract are then added, and mixing is continued until the composition is homogenous, generally at least 30-45 minutes. Next, the packaging is filled. While there exist several options for deodorant packaging, including bottom-filled and top-filled, the inventor has found that top-filled packages provide the best stability.

Therefore the next step following the mixing of all ingredients is the filling of packaging. While agitating the bulk mixture and maintaining the temperature, appropriate volumes of the mixture are poured into the top of appropriate empty plastic deodorant containers. The deodorant composition in the container is then cooled slightly, and an internal cap is added so that the top of the solidified deodorant will form a domed shape. The composition is then cooled further until it is in a solid state, then covered with a lid. The products are then ready for labelling, packing, and shipping. Following the above procedure, a natural deodorant solid stick product having a domed top is formed by a method of top-filling. This product further displays excellent qualities of stability, as revealed in the 12-week stability data presented in FIGS. 6 and 7.

Figure 6:
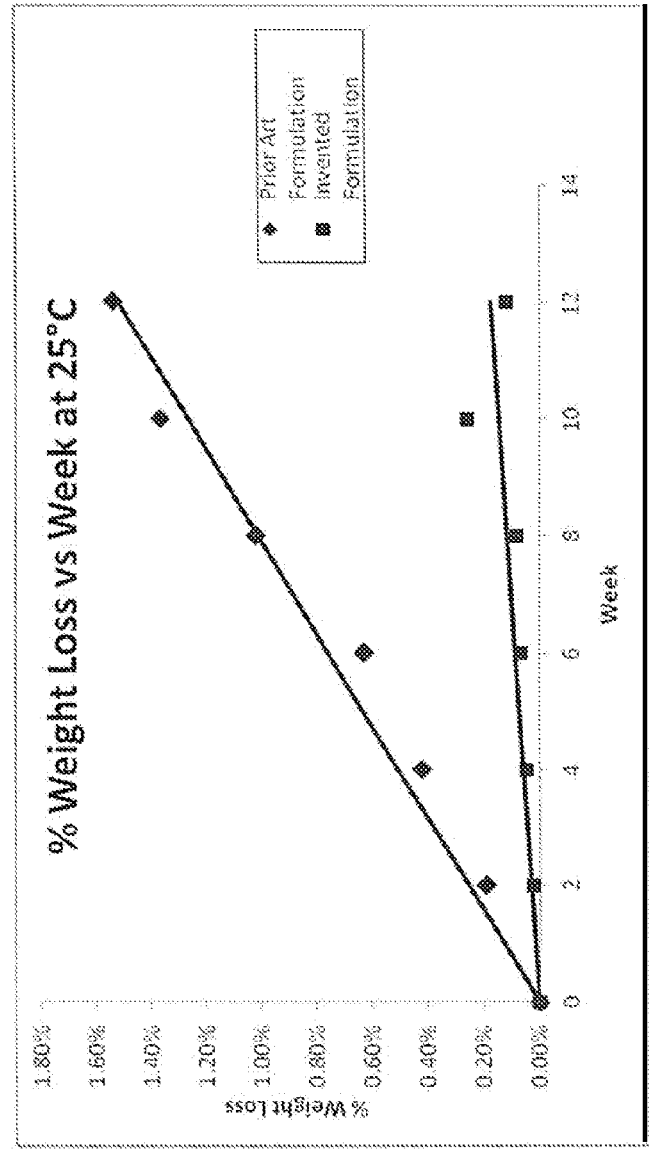
FIG. 6 shows the results of a 12-week stability test at 25° C. (approximately room temperature), for a top filled, domed deodorant product made in accordance with the formula in FIG. 1, as contrasted to a comparable prior art deodorant formulation.

FIG. 6 is a summary of a 12-week stability test. In terms of the invented formulation, the ingredient quantities set out in FIG. 1 were mixed, and deodorant sticks prepared in accordance with the manufacturing method described above. The containers were weighed at the beginning of the test in order to provide a baseline, and samples were subsequently incubated at 25° for a total of 12 weeks each. Every two weeks, a visual inspection was done of each deodorant stick inside the containers. Each container including the deodorant stick was then weighed, and the weight and percentage weight loss recorded.

At each visual inspection over the 12 weeks, it was observed that there was no moisture sitting on the surface of the deodorant product, nor was there softening of the surface. The recorded weight loss was therefore assessed as corresponding to the amount of moisture that had condensed on the surface of the stick and evaporated.

The same procedure was followed for a prior art formulation available as a control. The prior art formulation had proportions of propanediol, glycerin, and water that are similar to those seen in the formulation of the present invention, and it also did not contain volatile alcohols which may readily evaporate. Therefore the weight loss comparison between the control and the invented formulation was assessed as a suitable comparison.

It is seen that at 25° C. there is a significant difference between weight loss at 12 weeks between the two formulations. The weight loss of the prior art control was more than ten-fold higher. The rate of weight loss over the 12 weeks was also much accelerated in the prior art control versus the invented formulation, as graphically demonstrated by the slope of the corresponding lines in the graphs. This data demonstrates that at 25° C., which approximates the room temperature at which deodorant products are likely to be stored for prolonged periods prior to and after sale, the invented formulation lasts much longer in terms of maintaining its weight when compared to a prior art formulation.

Figure 7:
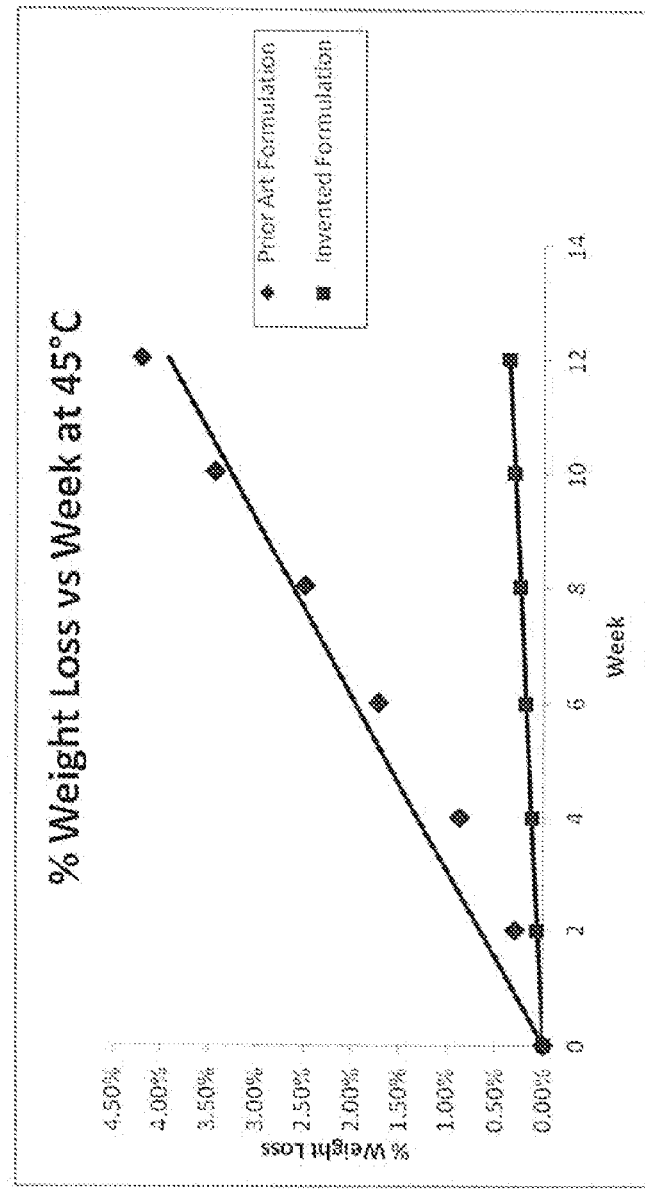
FIG. 7 shows the results of a 12-week stability test at 45° C. for a top filled, domed deodorant product made in accordance with the formula in FIG. 1, as contrasted to a comparable prior art deodorant formulation.

Similar results were seen at the higher temperature of 45° C., as set out in FIG. 7. All conditions and parameters described above in association with the FIG. 6 data were maintained, the only difference being the temperature setting of 45° C. instead of 25° C. Again, at 12 weeks, there was more than a ten-fold difference in weight of the incubated control versus the invented formulation. The rate of weight loss was similarly accelerated for the control versus the invented formulation.

This difference in weight loss translates to a significant difference in stability of the solid, deodorant product, when made in accordance with the method of top-filling described above. Such features of stability are highly advantageous to a commercial deodorant product, particularly when combined with good efficacy which extends to at least 24 hours.

As set out previously, a person of skill in the art may make variations of the formulations based on the variety of ingredients available in the prior art, as described above. It should further be noted that when an amount, concentration or other parameter is given as a range or a list of upper and lower preferable values, it is to be understood as disclosing all ranges formed from any pair of any upper and lower limit. Where a range of numerical values is recited, unless otherwise stated, the range includes the endpoints thereof.

While the invention has been described with reference to specific embodiments thereof, it will be appreciated that numerous variations, modifications, and embodiments are possible. All such variations, modifications and embodiments are to be regarded as being within the spirit and scope of the invention.

What is claimed is the following:

1. A deodorant composition, comprising by weight, based on the total weight of the composition: from about 30% to about 60% of propanediol; from about 1.5% to about 3% of zinc ricinoleate; from about 0.1% to about 2% of grapefruit seed extract; from about 0.05% to about 0.2% of sodium bicarbonate; from about 20% to about 40% of glycerin; from out 5% to about 10% of a gelling agent; from about 0.5% of polyglyceryl-3-caprate; and from about 0.9% of sucrose cocoate, wherein the application of said composition results in odour reduction, said odour reduction continuing at least 8 hours following said application to a level of about 25% reduction in odour as compared to an untreated control.

2. The deodorant composition according to claim 1, wherein said gelling agent is selected from the group consisting of sodium stearate, potassium stearate, and mixtures thereof.

3. The deodorant composition according to claim 2, wherein the gelling agent is sodium stearate.

4. The deodorant composition according to claim 3, wherein the sodium stearate is provided in an amount of about 8% by weight of the total composition.

5. The deodorant composition according to claim 1, in which the propanediol is provided in an amount of about 30% by weight of the total composition.

6. The deodorant composition according to claim 1, in which the zinc ricinoleate is provided in an amount of about 2.5% by weight of the total composition.

7. The deodorant composition according to claim 1, in which the grapefruit seed extract is provided in an amount of about 0.1% by weight of the total composition.

8. The deodorant composition according to claim 1, in which the sodium bicarbonate is provided in an amount of about 0.1 by weight of the total composition.

9. The deodorant composition according to claim 1, further comprising about 0.9% of silica.

10. The deodorant composition according to claim 1, further comprising about 0.2% of allantoin.

11. The deodorant composition according to claim 1, further comprising about 0.9% of corn starch.

12. A deodorant composition, comprising by weight, based on the total weight of the composition: from about 30% of propanediol; from about 2.5% of zinc ricinoleate; from about 0.1% of grapefruit seed extract; from about 0.1% of sodium bicarbonate; from about 30% of glycerin; from about 8% of sodium stearate; from about 0.5% of polyglyceryl-3-caprate; from about 0.9% of sucrose cocoate; from about 0.9% of silica; from about 0.2% of allantoin; and from about 0.9% of corn starch, wherein the application of said composition results in odour reduction said odour reduction continuing at least 8 hours following said application to a level of about 25% reduction in odour as compared to an untreated control.

13. A deodorant stick product comprising the deodorant composition of claim 12 and a deodorant container, wherein the deodorant composition is poured into the deodorant container from the top of said deodorant container and molded with a domed top.

14. The deodorant stick product according to claim 13, wherein said deodorant stick product shows a cumulative weight loss of 0.12% or less when stored for 12 weeks at 25° C.

15. The deodorant stick product according claim 13, wherein said deodorant stick product slaws a cumulative weight loss of 0.36% or less when stored for 12 weeks at 45° C.

16. The deodorant composition of claim 1, wherein said odour reduction continues at 16 hours following said application to a level of about 25% reduction in odour as compared to an untreated control.

17. The deodorant composition of claim 12, wherein said odour reduction continues at 16 hours following said application to a level of about 25% reduction in odour as compared to an untreated control.

18. The deodorant composition of claim 1, wherein said odour reduction continues at 24 hours following said application to a level of about 27% reduction in odour as compared to an untreated control.

19. The deodorant composition of claim 12, wherein said odour reduction continues at 24 hours following said application to a level of about 27% reduction in odour as compared to an untreated control.

* * * * *